United States Patent [19]
McDonough et al.

[11] Patent Number: 5,780,219
[45] Date of Patent: Jul. 14, 1998

[54] NUCLEIC ACID AMPLIFICATION OLIGONUCLEOTIDES AND PROBES TO HUMAN HEPATITIS B VIRUS

[75] Inventors: Sherrol H. McDonough, San Diego; Timothy J. Fultz, Martinez, both of Calif.

[73] Assignee: Gen-Probe Incorporated, San Diego, Calif.

[21] Appl. No.: 371,583

[22] Filed: Jan. 12, 1995

Related U.S. Application Data

[63] Continuation of Ser. No. 879,684, May 6, 1992, abandoned, which is a continuation-in-part of Ser. No. 550,837, Jul. 10, 1990, Pat. No. 5,480,784, which is a continuation-in-part of Ser. No. 379,501, Jul. 11, 1989, abandoned.

[51] Int. Cl.$^6$ .............................. C12Q 1/68; C07H 21/04
[52] U.S. Cl. .............................. 435/5; 435/6; 435/69.1; 435/91.2; 435/172.3; 436/501; 436/86; 536/23.1; 536/24.1; 536/24.3; 536/24.31; 536/24.32; 536/24.33; 935/77; 935/78
[58] Field of Search ..................... 435/5, 6, 69.1, 435/91.2, 172.3, 810; 436/501, 86; 536/22.1, 23.1, 24.1, 24.3, 33; 935/77, 78

[56] References Cited

U.S. PATENT DOCUMENTS

| | | | |
|---|---|---|---|
| 4,446,237 | 5/1984 | Berninger | 436/504 |
| 4,562,159 | 12/1985 | Shafritz | 436/501 |
| 4,683,195 | 7/1987 | Mullis et al. | 435/6 |
| 5,034,315 | 7/1991 | Jensen et al. | 435/6 |
| 5,079,351 | 1/1992 | Sninsky et al. | 536/27 |
| 5,155,216 | 10/1992 | Mock et al. | 536/24 |
| 5,399,491 | 3/1995 | Kacian et al. | 435/91.21 |
| 5,480,784 | 1/1996 | Kacian et al. | 435/91.21 |

FOREIGN PATENT DOCUMENTS

| | | |
|---|---|---|
| 0145356 | 6/1985 | European Pat. Off. . |
| 366448 | 5/1990 | European Pat. Off. . |
| 408295 | 1/1991 | European Pat. Off. . |
| WO85/03951 | 9/1985 | WIPO . |
| WO89/04375 | 5/1989 | WIPO . |
| WO90/13667 | 11/1990 | WIPO . |
| 9101384 | 7/1991 | WIPO . |
| WO91/10746 | 7/1991 | WIPO . |

OTHER PUBLICATIONS

Brunetto et al., "Wild-type and e antigen-minus hepatitis B viruses and course of chronic hepatitis", *Proc. Natl. Acad. Sci. USA* 88:4186–4190 (1991).

Brunetto et al., "Does HBeAg Minus HBV Modify the Course of HDV Superinfection?", *Prog. Clin. Biol. Res.* 364:211–216 (1991).

Fiordalisi et al., "High Genomic Variability in the Pre-C Region of Hepatitis B Virus in Anti–HBe, HBV DNA–Positive Chronic Hepatitis", *Journal of Medical Virology* 31:297–300 (1990).

Kaneko et al., "Detection of serum hepatitis B virus DNA in patients with chronic hepatitis using the polymerase chain reaction assay", *Proc. Natl. Acad. Sci. USA* 86:312–316 (1989).

Keller et al., "Detection of Hepatitis B Virus DNA in Serum by Polymerase Chain Reaction Amplification and Microtiter Sandwich Hybridization", *Journal of Clinical Microbiology* 28(6):1411–1416 (1990).

Larzul et al., "Detection of hepatitis B virus sequences in serum by using in vitro enzymatic amplification", *Journal of Virological Methods* 20:227–237 (1988).

Liang et al., "Characterization and Biological Properties of a Hepatitis B Virus Isolated from a Patient without Hepatitis B Virus Serologic Markers", *Hepatology* 12(2):204–212 (1990).

Liaw et al., "Incidence, Determinants and Significance of Delayed Clearance of Serum HBsAg in Chronic Hepatitis B Virus Infection: A Prospective Study", *Hepatology* 13(4):627 (1991).

Lo et al., "In vitro amplification of hepatitis B virus sequence from liver tumour DNA and from paraffin wax embedded tissues using the polymerase chain reaction", *Journal of Clinical Pathology* 42:840–846 (1989).

Pao et al., "Serum Hepatitis B Virus DNA in Hepatitis B Virus Seropositive and Seronegative Patients with Normal Liver Function", *Clinical Microbiology and Clinical Chemistry* 95(4):591–596 (1991).

Pasquinelli et al., "Hepatitis B Virus Infection of Peripheral Blood Mononuclear Cells Is Common in Acute and Chronic Hepatitis", *Journal of Medical Virology*, 31:135–140 (1990).

Seelig et al., "Hachweis von Hepatitis–B–Virus–DNA mit der Polymerase–Kettenreaktion", *Dtsch. Med. Wschr.* 115(35):1307–1312 (1990).

Sumzazki et al., "Detection of Hepatitis B Virus in Serum Using Amplification of Viral DNA by Means of the Polymerase Chain Reaction", *Journal of Medical Virology* 27:304–308 (1989).

Theilmann et al., "Detection of HBV DNA in HBsAg–positive sera after amplification using the polymerase chain reaction", *Liver* 9:322–328 (1989).

Urdea et al., "A novel method for the rapid detection of specific nucleotide sequences in crude biological samplpes without blotting or radioactivity; application to the analysis of hepatitis B virus in human serum", *Gene* 61:253–264 (1987).

Baginski et al., "Detection of Hepatitis B Virus", *PCR Protocols* 348–355 (1990).

Krogsgaard, "Hepatitis B virus DNA in serum. Applied molecular biology in the evaluation of hepatitis B infection", *Liver* 8:257–283 (1988).

Jackson, "Polymerase Chain Reaction Assay for Detection of Hepatitis B Virus", *American Journal of Clinical Pathology* 95(4):442–444 (1991).

(List continued on next page.)

*Primary Examiner*—Ardin H. Marschel
*Attorney, Agent, or Firm*—Lyon & Lyon LLP

[57] ABSTRACT

Amplification oligonucleotides and hybridization assay probes specific for Human Hepatitis B Virus.

57 Claims, No Drawings

OTHER PUBLICATIONS

Valenzuela et al., "Nucleotide sequence of the gene coding for the major protein of hepatitis B virus surface antigen", *Nature* 280:815–819, 1979.

Fujiyama et al., "Cloning and Structural Analysis of Hepatitis B Virus DNAs, Subtype ADR", *Nucleic Acids Research* 11:4601–4610, 1983.

Pasek et al., "Hepatitis B Virus Genes and Their Expression in *E. coli*", *Nature* 282:575–579, 1979.

Patrick Charnay et al., "Localization on the Viral Genome and Nucleotide Sequence of the Gene Coding for the Two Major Polypeptides of the Hepatitis B Surface Antigen (HBs Ag)," *Nucleic Acids Research*, 7(2):335–347 (1979).

Hiroaki Okamoto et al., "Nucleotide Sequence of a Cloned Hepatitis B Virus Genome, Subtype ayr: Comparison with Genomes of the Other Three Subtypes," *J. Gen. Virol.*, 67:2305–2314 (1986).

Francis Galibert et al., "Nucleotide sequence of the Hepatitis B Virus Genome (Subtype ayw) Cloned in *E. Coli*," *Nature*, 281(25):646–650 (1979).

Ono et al. (1983) Nuc. Acids Res., vol. 11, No. 6, pp. 1747–1757.

Muesing et al. (1985) Nature, vol. 313, pp. 450–458.

Murakawa et al. (1988) DNA, vol. 7, No. 4, pp. 287–295.

5,780,219

SEQUENCE LISTING ( 1 ) GENERAL INFORMATION:

( i i i ) NUMBER OF SEQUENCES: 16

( 2 ) INFORMATION FOR SEQ ID NO: 1:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) SEQUENCE DESCRIPTION: SEQ ID NO: 1:

GAGGCATAGC AGCAGGATGA AGAGG                                            2 5

( 2 ) INFORMATION FOR SEQ ID NO: 2:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) SEQUENCE DESCRIPTION: SEQ ID NO: 2:

GGGCGCACCT CTCTTTACGC GG                                               2 2

( 2 ) INFORMATION FOR SEQ ID NO: 3:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) SEQUENCE DESCRIPTION: SEQ ID NO: 3:

GGTCCCCTAG AAGAAGAACT CCCTCG                                           2 6

( 2 ) INFORMATION FOR SEQ ID NO: 4:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) SEQUENCE DESCRIPTION: SEQ ID NO: 4:

GGT TATCGCTGGA TGTGTCTGCG GC                                           2 5

( 2 ) INFORMATION FOR SEQ ID NO: 5:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) SEQUENCE DESCRIPTION: SEQ ID NO: 5:

GAGGACAAAC GGGCAACATA CCTTG                                            2 5

( 2 ) INFORMATION FOR SEQ ID NO: 6:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) SEQUENCE DESCRIPTION: SEQ ID NO: 6:

TCCTGGAATT AGAGGACAAA CGGGC    25

( 2 ) INFORMATION FOR SEQ ID NO: 7:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 7:

TCCTGGAATT AGAGGATAAA CGGGC    25

( 2 ) INFORMATION FOR SEQ ID NO: 8:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 8:

CGTCCTTTGT TTACGTCCCG TC    22

( 2 ) INFORMATION FOR SEQ ID NO: 9:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 9:

GCACACGGAC CGGCAGATGA GAAGGC    26

( 2 ) INFORMATION FOR SEQ ID NO: 10:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 10:

CACCAAATGC CCCTATCTTA TCAACACTTC CGG    33

( 2 ) INFORMATION FOR SEQ ID NO: 11:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 11:

CCCGAGATTG AGATCTTCTG CGAC    24

( 2 ) INFORMATION FOR SEQ ID NO: 12:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 12:

CGAGATTGAG ATCTTCTGCG ACGCG                                              25

( 2 ) INFORMATION FOR SEQ ID NO: 13:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 13:

AATTTAATAC GACTCACTAT AGGGAGA                                            27

( 2 ) INFORMATION FOR SEQ ID NO: 14:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 14:

CCTCTTCATC CTGCTGCTAT GCCTC                                              25

( 2 ) INFORMATION FOR SEQ ID NO: 15:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 15:

CCGCGTAAAG AGAGGTGCGC CC                                                 22

( 2 ) INFORMATION FOR SEQ ID NO: 16:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 16:

CGAGGGAGTT CTTCTTCTAG GGGACC                                             26

1

NUCLEIC ACID AMPLIFICATION OLIGONUCLEOTIDES AND PROBES TO HUMAN HEPATITIS B VIRUS

This application is a continuation of U.S. application Ser. No. 07/879,684, filed May 6, 1992, abandoned, which is a continuation-in-part of U.S. application Ser. No. 07/550,837, filed Jul. 10, 1990, issued as U.S. Pat. No. 5,480,784 on Jan. 2, 1996, which is a continuation-in-part of U.S. application Ser. No. 07/379,501, filed Jul. 11, 1989, abandoned.

FIELD OF THE INVENTION

This invention relates to the design and construction of amplification oligonucleotides and probes to Human Hepatitis B Virus, which allow detection of the organism in a test sample.

BACKGROUND OF THE INVENTION

Laboratory diagnosis of Hepatitis B Virus infection in humans is currently performed by demonstration of the presence of viral antigens (HBsAg, HBcAg and HBeAg), or their respective antibodies, in serum. Detection of Hepatitis B Virus DNA by nucleic acid hybridization is a more sensitive method for detection of virus in several clinical stages (Krogsgaard, *Liver* 8:257–283, 1988). Direct hybridization, however, lacks adequate sensitivity to detect HBV DNA in some patients, as shown by assay of patient samples following a nucleic acid amplification step such as the polymerase chain reaction™ (See, Kaneko et al., 1989, *Proc. Natl. Acad. Sci. U.S.A.* 86:312–316; Larzul et al., 1988, *J. Virol. Meth.* 20:227–237; Sumazaki et al., 1989; *J. Med. Virol.* 27:304–308; and Theilman et al., 1989 *Liver* 9:322–328. Relevant references describing amplification primers and detection probes for Human Hepatitis B Virus include the following, none of which are admitted to be prior art to the claimed invention: Seelig et al., *Deutsch Med Wochenschr* 115:1307–1312, 1990; Brunetto et al., *Proc. Natl. Acad. Sci., USA* 88:4186–4190, 1991; Brunetto et al., *Prog. Clin. Biol. Res.* (U.S.) 364:211–216, 1991; Fiordalisi et al., *J. Med. Virol.* 31:297–300, 1990; Liang et al., *Hepatology* 12(2)204–212, 1990; Lo et al., *J. Clin. Pathol.* 42:840–846, 1989; Sumazaki et al., *J. Med. Virol.* 27:304–308, 1989; PCR protocols, 1990, chapter on HBV; Liaw et al., *Hepatology* 13(4):627–631, 1991; Pao et al., *Am. J. Clin. Pathol.* 95(4):591–596, 1991; Keller et al., *J. Clin. Microbiol.* 28(6):1411–1416, 1990; Pasquinelli et al., *J. Med. Virol.* 31:135–140, 1990; Musso, Lanthanide chelate-tagged nucleic acids probes, PCT/US88/03735; Urdea, Improved amplified nucleic acid hybridization assays for HBV, PCT/US90/02049; Urdea, et al. *Gene* 61:253–264, 1987; and Urdea, DNA-Dependent RNA polymerase transcripts as reporter molecules for signal amplification in nucleic acid hybridization assays, PCT/US91/00213.

SUMMARY OF THE INVENTION

This invention discloses and claims novel amplification oligonucleotides and detection probes for the detection of Human Hepatitis B Virus. These probes detect unique sequences in the Human Hepatitis B Virus genome, and are capable of distinguishing between the Human Hepatitis B Virus and its known closest phylogenetic neighbors. These amplification oligonucleotides and probes may be used in an assay for the detection and/or quantitation of Human Hepatitis B Virus nucleic acid.

Thus, in a first aspect, the invention features hybridization assay probes able to distinguish Hepatitis B Virus from other viruses found in human blood or tissues, and amplification oligonucleotides able to selectively amplify Human Hepatitis B Virus nucleic acid. Specifically, the probe is a nucleotide polymer which hybridizes to the nucleic acid of HBV corresponding to (a) the 25 bases 403–427 of HBV sequence adw, (Ono et al. 1983, *Nuc. Acids Res.* 11(6):1747–1757, where base one is the first T in the EcoRI restriction endonuclease recognition sequence, (b) 22 bases corresponding to bases 1522–1543 of HBV adw sequence, or (c) 26 bases corresponding to bases 2367–2392 of HBV adw sequence, or a nucleotide polymer complementary thereto; i.e., the oligonucleotide comprises, consists essentially of, or consists of one of the sequences (reading 5'to 3')

(SEQ ID NO: 1) GAGGCATAGCAGCAGGATGAAG AGG, (SEQ ID NO: 2) GGGCGCACCTCTCTTTACGCGG, (SEQ ID NO: 3) GGTCCCCTAGAAGAAGAACTCC CTCG, or oligonucleotides complementary thereto.

By "consists essentially of" is meant that the probe is provided as a purified nucleic acid which hybridizes under stringent hybridizing conditions with the desired target nucleic acid and not with other related targets in other virus nucleic acids, or in human nucleic acid. Such a probe may be linked to other nucleic acids which do not affect such hybridization. Generally, it is preferred that the probe be of between 15 and 100 (most preferably between 20 and 50) bases in size. It may, however, be provided in a vector.

In related aspects, the invention features a nucleotide polymer which specifically hybridizes under stringent hybridization conditions to the above oligonucleotides, a nucleic acid hybrid formed with the above oligonucleotides, and a nucleic acid sequence substantially complementary thereto. Such hybrids are useful because they allow the specific detection of viral nucleic acid, i.e., they represent the specific hybridization of probes of this invention with target nucleic acid.

In another aspect, the invention features amplification oligonucleotides useful for specific detection of Human Hepatitis B Virus in an amplification assay. The amplification oligonucleotides are complementary to a conserved region of HBV genomic nucleic acid and are nucleotide polymers able to hybridize to the nucleic acid of HBV corresponding to HBV sequence adw bases 365 to 389, bases 455 to 479, bases 466 to 490, bases or corresponding bases 1415 to 1436, bases 1557 to 1587, bases 2301 to 2333, bases 2418 to 2442, or bases 2421 to 2444.

Specifically, such oligonucleotides consist, comprise or consist essentially of these selected from (reading 5' to 3'):

SEQ. ID. NO. 4:(X)GGTTATCGCTGGATGTGTCTG CGGC,

SEQ. ID. NO. 5:(X)GAGGACAAACGGGCAACATA CCTTG,

SEQ. ID. NO. 6:(X)TCCTGGAATTAGAGGACAAA CGGGC,

SEQ. ID. NO. 7:(X)TCCTGGAATTAGAGGATAAAC GGGC,

SEQ. ID. NO. 8:(X)CGTCCTTTGTTTACGTCCCGTC,

SEQ. ID. NO. 9:(X)GCACACGGACCGGCAGATGA GAAGGC,

SEQ. ID. NO. 10:(X)CACCAAATGCCCCTATCTTAT CAACACTTCCGG,

SEQ. ID. NO. 11:(X)CCCGAGATTGAGATCTTCTG CGAC, and

SEQ. ID. NO. 12:(X)CGAGATTGAGATCTTCTGCG ACGCG where (X) is nothing or a 5' oligonucleotide sequence that is recognized by an enzyme RNA polymerase (including but not limited to the promoter sequence for T7, T3, or SP6 RNA polymerase), which enhances initiation or elongation of RNA transcription by an RNA polymerase. One example of X includes the sequence (SEQ. ID. NO. 13) 5'-AATTTAATACGACTCACTATAGGGAGA-3'.

These amplification oligonucleotides are used in a nucleic acid amplification assay such as the polymerase chain reaction or an amplification reaction using RNA polymerase, DNA polymerase and RNaseH or its equivalent, as described by Kacian and Fultz, supra, and by Sninsky et al. U.S. Pat. No. 5,079,351, both hereby incorporated by reference herein.

The amplification oligonucleotides and probes of this invention offer a rapid, non-subjective method of identification and quantitation of a sample for specific sequences unique to all strains of HBV.

Other features and advantages of the invention will be apparent from the following description of the preferred embodiments thereof, and from the claims.

DESCRIPTION OF THE PREFERRED EMBODIMENTS

We have discovered particularly useful DNA probes complementary to particular nucleic acid sequences of Human Hepatitis B Virus. Furthermore, we have successfully used those probes in a specific assay for the detection of Human Hepatitis B Virus, distinguishing it from the known and presumed most closely related taxonomic or phylogenetic neighbors found in human blood or tissues.

We have also identified particularly useful amplification oligonucleotides which are complementary to the Human Hepatitis B Virus nucleic acid, and have used these oligonucleotides, e.g., as primers or promoter-primer combinations (i.e., a primer having a promoter sequence attached), to amplify the nucleic acid of Human Hepatitis B Virus, allowing its direct detection in a serum sample.

Useful guidelines for designing amplification oligonucleotides and probes with desired characteristics are described herein. The optimal sites for amplifying and probing contain two, and preferably three, conserved regions greater than about 15 bases in length, within about 350 bases, and preferably within 150 bases, of contiguous sequence. The degree of amplification observed with a set of primers or primer/splice templates depends on several factors, including the ability of the oligonucleotides to hybridize to their complementary sequences and their ability to be extended enzymatically. Because the extent and specificity of hybridization reactions are affected by a number of factors, manipulation of those factors will determine the exact sensitivity and specificity of a particular oligonucleotide, whether perfectly complementary to its target or not. The importance and effect of various assay conditions are known to those skilled in the art as described in Hogan et al. Nucleic Acid Probes for Detection and/or Quantitation of non-Viral Organisms. U.S. Ser. No. 07/806,929, filed Dec. 11, 1991, and Milliman, Nucleic Acid Probes to Haemophilus influenzae, U.S. Ser. No. 07/690,788, filed Apr. 25, 1991 assigned to the same assignee as the present application and hereby incorporated by reference herein.

The length of the target nucleic acid sequence and, accordingly, the length of the probe sequence can be important. In some cases, there may be several sequences from a particular region, varying in location and length, which will yield probes with the desired hybridization characteristics. In other cases, one sequence may be significantly better than another which differs merely by a single base. While it is possible for nucleic acids that are not perfectly complementary to hybridize, the longest stretch of perfectly homologous base sequence will normally primarily determine hybrid stability. While oligonucleotide probes of different lengths and base composition may be used, oligonucleotide probes preferred in this invention are between about 10 to 50 bases in length and are sufficiently homologous to the target nucleic acid. We have found that optimal primers have target-binding regions of 18–28 bases, with a predicted Tm to target of 65° C.

Amplification oligonucleotides or probes should be positioned so as to minimize the stability of the oligomer: nontarget (i.e., nucleic acid with similar sequence to target nucleic acid) nucleic acid hybrid. It is preferred that the amplification oligomers and detection probes are able to distinguish between target and non-target sequences. In designing probes, the differences in these Tm values should be as large as possible (e.g., at least 2° C. and preferably 5° C).

Regions of the nucleic acid which are known to form strong internal structures inhibitory to hybridization are less preferred. Likewise, probes and amplification oligonucleotides with extensive self-complementarity should be avoided.

The degree of non-specific extension (primer-dimer or non-target copying) can also affect amplification efficiency, therefore primers are selected to have low self- or cross-complementarity, particularly at the 3' ends of the sequence. Long homopolymer tracts and high GC content are avoided to reduce spurious primer extension. Computer programs are available to aid in this aspect of the design.

Hybridization is the association of two single strands of complementary nucleic acid to form a hydrogen bonded double strand. It is implicit that if one of the two strands is wholly or partially involved in a hybrid that it will be less able to participate in formation of a new hybrid. By designing a probe so that a substantial portion of the sequence of interest is single stranded, the rate and extent of hybridization may be greatly increased. If the target is an integrated genomic sequence then it will naturally occur in a double stranded form, as is the case with the product of the polymerase chain reaction (PCR). These double stranded targets are naturally inhibitory to hybridization with a probe and require denaturation prior to the hybridization step. Probes of this invention are directed to the major product of an amplification system, which is single-stranded RNA. Finally, there can be intramolecular and intermolecular hybrids formed within a probe if there is sufficient self complementarity. Such structures can be avoided through careful probe design. Computer programs are available to search for this type of interaction.

Once synthesized, selected oligonucleotides may be labelled by any of several well known methods. Sambrook et al., 2 *Molecular Cloning* 11 (2d ed. 1989). Useful labels include radioisotopes as well as non-radioactive reporting groups. We currently prefer to use acridinium esters.

Oligonucleotide/target hybrid melting temperature may be determined by isotopic methods well known to those skilled in the art. It should be noted that the Tm for a given hybrid will vary depending on the hybridization solution being used. Sambrook et al., supra.

Rate of hybridization may be measured by determining the $C_0t_{1/2}$. The $C_0t_{1/2}$ is found graphically by standard procedure.

The following example sets forth oligonucleotide probes complementary to a unique nucleic acid sequence from a target organism, and their use in a hybridization assay.

EXAMPLE

Probes specific for Human Hepatitis B Virus were identified by comparison of sequences obtained from the published database GenBank. The following sequences were characterized and shown to be specific for Human Hepatitis B Virus:

(SEQ ID NO: 1) GAGGCATAGCAGCAGGATGAA-GAGG (probe 1)

(SEQ ID NO: 2) GGGCGCACCTCTCTTTACGCGG (probe 2)

(SEQ ID NO: 3) GGTCCCCTAGAAGAAGAACTC-CCTCG (probe 3)

Phylogenetically near neighbors including Woodchuck Hepatitis Virus and Ground Squirrel Hepatitis Virus were used as comparisons with the sequence of Human Hepatitis B Virus.

To demonstrate the reactivity and specificity of the probes for Human Hepatitis B Virus, they were used in a hybridization assay. The probes were first synthesized with a non-nucleotide linker, then labelled with a chemiluminescent acridinium ester as described in EPO Patent Application No. PCT/US88/03361, entitled "Acridinium Ester Labeling and Purification of Nucleotide Probes filed Oct. 5, 1988. The acridinium ester attached to unhybridized probe is rendered non-chemiluminescent under mild alkaline conditions, while the acridinium ester attached to hybridized probe is relatively resistant. Thus, it is possible to assay for hybridization of acridinium ester-labelled probe by incubation with an alkaline buffer, followed by detection of chemiluminescence in a luminometer. Results are given in RLU, the quantity of photons emitted by the labelled-probe measured by the luminometer. The conditions of hybridization, hydrolysis and detection are described in Arnold, et al., 35 Clin. Chem. 1588, 1989.

In the following experiment, DNA prepared from clones containing full or partial sequences of the viruses was assayed. An example of such a method is provided by Sambrook et al., supra. The source of DNA for the clones was as follows; Human Hepatitis B Virus serotype ADW, obtained from ATCC #45020; Human Immunodeficiency Virus type 1, BH10(Ratner et al., Nature 312:277-284, 1985); Human Immunodeficiency Virus type 2 NIHZ (Zagury et al., Proc. Natl. Acad. Sci. USA 85:5941-5945, 1988), Human T-cell leukemia virus type 1 pMT-2, (Clarke et al., Nature 305:60-62, 1983); and Human T-cell leukemia virus type 2 (Shimotohmo et al., Proc. Natl. Acad. Sci. U.S.A. 82:3101-3105, 1985). An RLU value greater than 3,000 RLU was a positive result; less than 3,000 RLU was a negative result.

The following data show that the probes do not cross react with DNA from closely related viruses found in human blood or tissues. The samples were also tested with a probe specific to each target. A positive signal from this probe provided confirmation of sample adequacy.

| Target | Probe 1 | Probe 2 | Probe 3 | Positive Control |
|---|---|---|---|---|
| HBV ADW 1.3, 1.8 kb BamHI fragments | 11,789 | 168,795 | 18,982 | — |
| HIV-1 9 kb SstI fragment | 429 | 2,788 | 272 | 98,314 |
| HIV-2 9 kb SstI fragment | 594 | 2,287 | 272 | 33,635 |
| HTLV-1 5' 4.6 kb SstI-BamHI fragment | 413 | 365 | 148 | 24,999 |
| HTLV-1 3' 4.4 kb XbaI-SstI fragment | 421 | 341 | 145 | 27,149 |
| HTLV-2 3.5 kb BamHI fragment | 554 | 324 | 153 | 47,879 |
| HTLV-2 5 kb BamHI fragment | 359 | 328 | 155 | 16,690 |

The above data confirm that the novel probes are capable of distinguishing Human Hepatitis B Virus from these viruses found in human serum.

To demonstrate the reactivity of the primers and probes for Human Hepatitis B virus, the following experiment was performed. Plasmid DNA containing the Human Hepatitis B Virus sequence was linearized with a restriction endonuclease, and added to amplification reactions using standard polymerase chain reaction conditions. Following amplification, the products were analyzed by hybridization protection assay.

| Primers | Target Level (Units) | RLU |
|---|---|---|
| Seq ID 4/7 | 1,000 | 25,737 |
| | 0 | 474 |
| Seq ID 8/9 | 1,000 | 36,278 |
| | 0 | 904 |
| Seq ID 10/12 | 1,000 | 152,306 |
| | 0 | 797 |

To show that the amplification oligomers also work in a transcription based amplification assay, patient samples were evaluated. Ten microliter plasma samples from patients (uninfected are termed "normal") were treated with ten microliters of 0.2N KOH at 95° C. for 15 minutes, then neutralized. A buffer containing reagents for amplification was added to a final concentration of 150 nM each primer, 88 mM imidazole, 55 mM glutamate, 2.5% PVP-40, 2 mM spermidine, 15 mM N-acetyl-cysteine, 6.25 mM rATP and rGTP, 2.5 mM rCTP and rUTP, 0.2 mM each of dTTP, DATP, dCTP and dGTP, 21 MM $MgCl_2$, 0.5 mM zinc acetate, 0.005% Triton X-100, 1200 U of MMLV reverse transcriptase, 200 U of T7 RNA polymerase and incubated at 36° C. for 3 hours. The entire reaction was analyzed by Hybridization Protection Assay as described above.

The results, in Relative Light Units, or RLU, are shown.

| Primers: | SEQ ID 4/7 | SEQ ID 8/9 | SEQ ID 10/12 |
|---|---|---|---|
| Probe: | 1 | 2 | 3 |
| Sample | | | |
| #1 | 221,521 | 22,981 | 1,151,234 |
| #2 | 243,659 | 580,709 | 1,544,800 |
| #3 | 283,827 | 119,153 | 1,526,431 |
| #4 | 12,988 | 7,953 | 749,369 |
| #5 | 277,533 | 145,727 | 1,502,496 |
| #6 | 266,310 | 107,026 | 1,458,598 |
| #7 | 245,661 | 142,530 | 1,504,906 |
| #8 | 301,941 | 149,795 | 1,455,712 |
| Normal #1 | 7,294 | 9,303 | 6,271 |
| Normal #2 | 6,590 | 6,164 | 4,404 |

The results shown are the average of three replicates. All of the positive clinical samples were detected with two of the primer pairs. The third primer pair detected all but one sample which contained low amounts of target. Optimization of amplification conditions is expected to increase RLU observed with each primer pair. Both normal serum samples gave <10,000 RLU in the assay.

Other embodiments are within the following claims.

We claim:

1. An oligonucleotide from 15 to 100 nucleotides in length comprising a sequence selected from the group consisting of:

(X) GAGGACAAACGGGCAACATACCTTG (SEQ ID NO: 5), (X) TCCTGGAATTAGAGGACAAACGGGC (SEQ ID NO: 6), (X) TCCTGGAATTAGAGGATAAACGGGC (SEQ ID NO: 7), (X) CGTCCTTTGTTTACGTCCCGTC (SEQ ID NO: 8), (X) CACCAAATGCCCCTATCTTATCAACACTTCCGG (SEQ ID NO: 10), (X) CCCGAGATTGAGATCTTCTGCGAC (SEQ ID NO: 11), (X) CGAGATTGAGATCTTCTGCGACGCG (SEQ ID NO: 12), where X is nothing or comprises an oligonucleotide sequence recognized by an RNA polymerase or which enhances initiation or elongation by an RNA polymerase.

2. A kit comprising an oligonucleotide from 15 to 100 nucleotides in length comprising a sequence selected from the group consisting of:

GGGCGCACCTCTCTTTACGCGG (SEQ ID NO: 2)

CGTCCCCTAGAAGAAGAACTCCCTCG (SEQ ID NO: 3)

(X) GAGGACAAACGGGCAACATACCTTG (SEQ ID NO: 5).

(X) TCCTGGAATTAGAGGACAAACGGGC (SEQ ID NO: 6).

(X) TCCTGGAATTAGAGGATAAACGGGC (SEQ ID NO: 7).

(X) CGTCCTTTGTTTACGTCCCGTC SEQ ID NO: 8).

(X) CACCAAATGCCCCTATCTTATCAACACTTCCGG (SEQ ID NO: 10).

(X) CCGAGATTGAGATCTTCTGCGAC (SEQ ID NO: 11).

(X) CGAGATTGAGATCTTCTGCGACGCG (SEQ ID NO: 12)

where X is nothing or comprises an oligonucleotide sequence recognized by an RNA polymerase or which enhances initiation or elongation by an RNA polymerase.

3. The kit of claim 2, wherein said kit comprises oligonucleotides from 15 to 100 nucleotides in length comprising the following sequences:

(X) GGTTATCGCTGGATGTGTCTGCGGC (SEQ ID NO: 4), (X) TCCTGGAATTAGAGGACAAACGGGC (SEQ ID NO: 6), and

GAGGCATAGCAGCAGGATGAAGAGG (SEQ ID NO: 1)

where X is nothing or comprises an oligonucleotide sequence recognized by an RNA polymerase or which enhances initiation or elongation by an RNA polymerase.

4. The kit of claim 2, wherein said kit comprises oligonucleotides from 15 to 100 nucleotides in length comprising the following sequences:

(X) CGTCCTTTGTTTACGTCCCGTC (SEQ ID NO: 8), (X) GCACACGGACCGGCAGATGAGAAGGC (SEQ ID NO: 9), and

GGGCGCACCTCTCTTTACGGCGG (SEQ ID NO: 2), where X is nothing or comprises an oligonucleotide sequence recognized by an RNA polymerase or which enhances initiation or elongation by an RNA polymerase.

5. The kit of claim 2, wherein said kit comprises oligonucleotides from 15 to 100 nucleotides in length comprising the following sequences;

(X)CACCAAATGCCCCTATCTTATCAACACTTCCGG (SEQ ID NO: 10), (X)CCCGAGATTGAGATCTTCTGCGAC (SEQ ID NO: 11), and GGTCCCCTAGAAGAAGAACTCCCTCG (SEQ ID NO: 3), where X is nothing or comprises an oligonucleotide sequence recognized by an RNA polymerase or which enhances initiation or elongation by an RNA polymerase.

6. An oligonucleotide from 15 to 100 nucleotides in length which is capable of hybridizing to a region of Human Hepatitis B Virus serotype ADW nucleic acid to form a detectable hybridization duplex under selective hybridization conditions, but does not hybridize to HIV-1 nucleic acid, HIV-2 nucleic acid, HTLV-1 nucleic acid, or HTLV-2 nucleic acid to form a detectable duplex under said selective hybridization conditions;

wherein said region consists of bases 2367–2392 of said Hepatitis B Virus or its fully complementary strand of the same length.

7. The oligonucleotide of claim 6 from 15 to 50 nucleotides in length.

8. The oligonucleotide of claim 6, wherein said oligonucleotide comprises a sequence fully complementary to at least 10 contiguous nucleotides of said region.

9. The oligonucleotide of claim 6 containing a detectable label.

10. The oligonucleotide of claim 9, wherein said detectable label is an acridinium ester.

11. The oligonucleotide of claim 8, wherein said sequence is SEQ. ID. NO. 3 or its fully complementary strand of the same length.

12. The oligonucleotide of claim 11 containing a detectable label.

13. The oligonucleotide of claim 12, wherein said detectable label is an acridinium ester.

14. A specifically detectable nucleic acid hybrid formed between the oligonucleotide of claim 6 and a region of Human Hepatitis B virus nucleic acid.

15. A specifically detectable nucleic acid hybrid formed between the oligonucleotide of claim 7 and a region of Human Hepatitis B virus nucleic acid.

16. A specifically detectable nucleic acid hybrid formed between the oligonucleotide of claim 8 and a region of Human Hepatitis B virus nucleic acid.

17. A specifically detectable nucleic acid hybrid formed between the oligonucleotide of claim 9 and a region of Human Hepatitis B virus nucleic acid.

18. A specifically detectable nucleic acid hybrid formed between the oligonucleotide of claim 10 and a region of Human Hepatitis B virus nucleic acid.

19. A specifically detectable nucleic acid hybrid formed between the oligonucleotide of claim 11 and a region of Human Hepatitis B virus nucleic acid.

20. An oligonucleotide from 15 to 100 nucleotides in length which is capable of hybridizing to a region of Human Hepatitis B Virus serotype ADW nucleic acid, wherein (a) said region is selected from the group consisting of bases 455–479 of said Hepatitis B Virus, bases 466–490 of said Hepatitis B Virus, bases 1415–1436 of said Hepatitis B Virus, bases 2301–2333 of said Hepatitis B Virus, bases 2418–2442 of said Hepatitis B Virus, and bases 2421–2444 of said Hepatitis B Virus; and (b) said oligonucleotide comprises a sequence fully complementary to at least 10 contiguous nucleotides of said region.

21. The oligonucleotide of claim 20, wherein said sequence is SEQ. ID. NO. 5.

22. The oligonucleotide of claim 20, wherein said sequence is SEQ. ID. NO. 6.

23. The oligonucleotide of claim 20, wherein said sequence is SEQ. ID. NO. 7.

24. The oligonucleotide of claim 20, wherein said sequence is SEQ. ID. NO. 8.

25. The oligonucleotide of claim 20, wherein said sequence is SEQ. ID. NO. 10.

26. The oligonucleotide of claim 20, wherein said sequence is SEQ. ID. NO. 11.

27. The oligonucleotide of claim 20, wherein said sequence is SEQ. ID. NO. 12.

28. The oligonucleotide of claim 20 which comprises, in the 5' upstream region, an oligonucleotide sequence which is recognizable by an RNA polymerase and enhances initiation or elongation by said RNA polymerase.

29. A composition for amplifying Human Hepatitis B Virus nucleic acid, comprising (a) a first oligonucleotide from 10 to 100 nucleotides in length which is capable of hybridizing to bases 365–389 of Human Hepatitis B Virus serotype ADW nucleic acid, and comprises a sequence fully complementary to at least 10 contiguous nucleotides from said bases 365–389; and (b) a second oligonucleotide from 10 to 100 nucleotides in length which is capable of hybridizing to the fully complementary strand of a region of Human Hepatitis B Virus serotype ADW nucleic acid, wherein said region is selected from the group consisting of bases 455–479 and bases 466–490 of said Hepatitis B Virus; and said second oligonucleotide comprises a sequence fully complementary to at least 10 contiguous nucleotides of said region.

30. The composition of claim 29, wherein said first oligonucleotide comprises SEQ. ID. NO. 4 and said second oligonucleotide comprises a sequence selected from the group consisting of SEQ. ID. NOs. 5, 6 and 7.

31. The composition of claim 29, further comprising a third oligonucleotide from 10 to 100 nucleotides in length comprising SEQ. ID. NO. 1 or its fully complementary strand of the same length.

32. The composition of claim 31, wherein said third oligonucleotide contains a detectable label.

33. The composition of claim 32, wherein said detectable label is an acridinium ester.

34. The compositon of claim 29, wherein at least one of said first oligonucleotide or said second oligonucleotide further comprises, in the 5' upstream region, an oligonucleotide sequence which is recognizable by an RNA polymerase and enhances initiation or elongation by said RNA polymerase.

35. A composition for amplifying Human Hepatitis B Virus nucleic acid, comprising (a) a first oligonucleotide from 10 to 100 nucleotides in length which is capable of hybridizing to bases 1415–1436 of Human Hepatitis B Virus serotype ADW nucleic acid, and comprises a sequence fully complementary to at least 10 contiguous nucleotides from said bases 1415–1436; and (b) a second oligonucleotide from 10 to 100 nucleotides in length which is capable of hybridizing to the fully complementary strand of bases 1557–1587 of Human Hepatitis B Virus serotype ADW nucleic acid, and comprises a sequence fully complementary to at least 10 contiguous nucleotides from said bases 1557–1587.

36. The composition of claim 35, wherein said first oligonucleotide comprises SEQ. ID. NO. 8 and said second oligonucleotide comprises SEQ. ID. NO. 9.

37. The composition of claim 35, further comprising a third oligonucleotide from 10 to 100 nucleotides in length comprising SEQ. ID. NO. 2 or its fully complementary strand of the same length.

38. The composition of claim 37, wherein said third oligonucleotide contains a detectable label.

39. The composition of claim 38, wherein said detectable label is an acridinium ester.

40. The compositon of claim 35, wherein at least one of said first oligonucleotide or said second oligonucleotide further comprises, in the 5' upstream region, an oligonucleotide sequence which is recognizable by an RNA polymerase and enhances initiation or elongation by said RNA polymerase.

41. A composition for amplifying Human Hepatitis B Virus nucleic acid, comprising (a) a first oligonucleotide from 10 to 100 nucleotides in length which is capable of hybridizing to bases 2301–2333 of Human Hepatitis B Virus serotype ADW nucleic acid, and comprises a sequence fully complementary to at least 10 contiguous nucleotides from said bases 2301–2333; and (b) a second oligonucleotide from 10 to 100 nucleotides in length which is capable of hybridizing to the fully complementary strand of a region of Human Hepatitis B Virus serotype ADW nucleic acid, wherein said region is selected from the group consisting of bases 2418–2442 and bases 2421–2444 of said Hepatitis B Virus; and said second oligonucleotide comprises a sequence fully complementary to at least 10 contiguous nucleotides of said region.

42. The composition of claim 41, wherein said first oligonucleotide comprises SEQ. ID. NO. 10 and said second oligonucleotide comprises SEQ. ID. NO. 11 or 12.

43. The composition of claim 41, further comprising a third oligonucleotide from 10 to 100 nucleotides in length comprising SEQ. ID. NO. 3 or its fully complementary strand of the same length.

44. The composition of claim 43, wherein said third oligonucleotide contains a detectable label.

45. The composition of claim 44, wherein said detectable label is an acridinium ester.

46. The composition of claim 41, wherein at least one of said first oligonucleotide or said second oligonucleotide further comprises, in the 5' upstream region, an oligonucleotide sequence which is recognizable by an RNA polymerase and enhances initiation or elongation by said RNA polymerase.

47. An oligonucleotide from 10 to 100 nucleotides in length which is capable of hybridizing to bases 403–427 of Human Hepatitis B Virus serotype ADW nucleic acid or its fully complementary strand of the same length to form a detectable hybridization duplex under selective hybridization conditions, but does not hybridize to HIV-1 nucleic acid, HIV-2 nucleic acid, HTLV-1 nucleic acid, or HTLV-2 nucleic acid to form a detectable duplex under said selective hybridization conditions.

48. The oligonucleotide of claim 47 from 15 to 50 nucleotides in length.

49. The oligonucleotide of claim 47, wherein said oligonucleotide comprises a sequence fully complementary to at least 10 contiguous nucleotides of said region.

50. The oligonucleotide of claim 47 containing a detectable label.

51. The oligonucleotide of claim 50, wherein said detectable label is an acridinium ester.

52. The oligonucleotide of claim 49, wherein said sequence is SEQ. ID. NO. 1 or its fully complementary strand of the same length.

53. The oligonucleotide of claim 52 containing a detectable label.

54. The oligonucleotide of claim 53, wherein said detectable label is an acridinium ester.

55. A specifically detectable nucleic acid hybrid formed between the oligonucleotide of claim 47 and a region of Human Hepatitis B virus nucleic acid.

56. A specifically detectable nucleic acid hybrid formed between the oligonucleotide of claim 48 and a region of Human Hepatitis B virus nucleic acid.

57. A specifically detectable nucleic acid hybrid formed between the oligonucleotide of claim 49 and a region of Human Hepatitis B virus nucleic acid.

\* \* \* \* \*